US009783514B2

(12) United States Patent
Cantat et al.

(10) Patent No.: US 9,783,514 B2
(45) Date of Patent: Oct. 10, 2017

(54) METHOD FOR PREPARING METHYLATED AMINES

(71) Applicant: Commissariat A L'Energie Atomique Et Aux Energies Alternatives, Paris (FR)

(72) Inventors: Thibault Cantat, Issy les Moulineaux (FR); Christophe Gomes, Antony (FR); Olivier Jacquet, Orsay (FR)

(73) Assignee: Commissariat A L'Energie Atomique Et Aux Energies Alternatives, Paris (FR)

( * ) Notice: Subject to any disclaimer, the term of this patent is extended or adjusted under 35 U.S.C. 154(b) by 64 days.

(21) Appl. No.: 14/404,865

(22) PCT Filed: Jun. 4, 2013

(86) PCT No.: PCT/IB2013/054599
§ 371 (c)(1),
(2) Date: Dec. 1, 2014

(87) PCT Pub. No.: WO2013/182991
PCT Pub. Date: Dec. 12, 2013

(65) Prior Publication Data
US 2015/0152072 A1 Jun. 4, 2015

(30) Foreign Application Priority Data

Jun. 5, 2012 (FR) ...................... 12 55234

(51) Int. Cl.
| | | |
|---|---|---|
| *C07D 295/00* | (2006.01) | |
| *C07C 209/28* | (2006.01) | |
| *C07D 211/14* | (2006.01) | |
| *C07D 295/04* | (2006.01) | |
| *C07D 295/02* | (2006.01) | |
| *C07C 217/82* | (2006.01) | |
| *C07B 43/04* | (2006.01) | |
| *C07B 59/00* | (2006.01) | |

(52) U.S. Cl.
CPC ............ *C07D 295/00* (2013.01); *C07B 43/04* (2013.01); *C07B 59/001* (2013.01); *C07B 59/002* (2013.01); *C07C 209/28* (2013.01); *C07C 217/82* (2013.01); *C07D 211/14* (2013.01); *C07D 295/02* (2013.01); *C07D 295/04* (2013.01); *C07B 2200/05* (2013.01)

(58) Field of Classification Search
None
See application file for complete search history.

(56) References Cited

PUBLICATIONS

Jacquet, Olivier. CO2 as a C1-building block for the catalytic methylation of amines. The Royal Society of Chemistry. 4, (2013), 2127-2131.*
Li, Yuehui. A General Catalytic Methylation of Amines Using Carbon Dioxide. Angew. Chem. Int. Ed. 2013, 52, 9568-9571.*
International Search Report and Written Opinion from International Application No. PCT/IB2013/054599 dated Aug. 29, 2013.
Salvatore R N et al.; "Efficient Cs2CO3-promoted Solution and Solid Phase Synthesis of Carbonates and Carbamates in the Presence of TBAI"; *Tetrahedron*, Elsevier Science Publishers, Amsterdam, NL; vol. 58, No. 17; Apr. 22, 2002; pp. 3329-3347; XP004349219.
Gredig S V et al.; "Palladium Catalyzed Synthesis of Methylamines from Carbon Dioxide, Hydrogen and Ammonia"; *Catalysis Letters*, Springer New York LLC, United States; vol. 46, No. 1/02; Jun. 1, 1997; pp. 49-55; XP000692742.
S. Ram et al.; "Rapid Reductive-Carboxylation of Secondary Amines. One Pot Synthesis of Tertiary N-methylated Amines"; *Tetrahedron Letters*; vol. 26, No. 44; Jan. 1, 1985; pp. 5367-5370; XP002690975.
S. Ram et al.; "Regio- and Chemoselective N-C Bond Formation Via Carbon Dioxide: A New Source of the Methyl Group"; *Synthetic Communications*; vol. 19, No. 20; Jan. 1, 1989; pp. 3561-3571; XP002690976.
S.T. Riduan et al.; "Conversion of Carbon Dioxide Into Methanol With Silanes Over N-heterocyclic Carbene Catalysts"; *Angewandte Chemie International Edition*; vol. 48; Jan. 1, 2009; pp. 3322-3325; XP002690977.
Morris A J et al.; *Accounts Chem. Res.*, 2009, 42 (1983).
Riduan S N et al.; *Angewandte Chemie-International Edition*, 2009, 48: 3322.
Sakakura T et al.; *Chem. Rev.*, 2007, 107: 2365.
Lawrence S et al.; Amines: Synthesis, Properties and Applications; *Cambridge University Press*; 2006.
Arpe H-J et al.; *Industrial Organic Chemistry*, Wiley-VCH, Weinheim; 1997.
Ali M F et al.; *Handbook of Industrial Chemistry—Organic Chemicals*, McGraw-Hill, New York; 2005.
Smith C L et al.; *Journal of Organometallic Chemistry*, 81 (1974) pp. 33-40.
Homer G D et al.; *Journal of the American Chemical Society*; 95, 23 (1973) pp. 7700-7707.
Spialter L et al.; *Journal of the American Chemical Society*; 93, 22 (1971) pp. 5682-5686.
West R; *Journal of the American Chemical Society* (1954) pp. 6015-6017.
Pleiss U et al.; "Synthesis and Applications of Isotopically Labelled Compounds"; vol. 7, *Wiley-WCH*; 2001.
Voges R et al.; "Preparation of Compounds Labeled with Tritium and Carbon-14"; *Wiley-WCH*, Chippenham (UK) 2009.
Kim Yong-Joo et al.; *J. Org. Chem.*; 1991, 56; pp. 4435-4439.
Kochina T A et al.; *Russian Journal of General Chemistry*; vol. 72, No. 8; 2002; pp. 1222-1224.

(Continued)

*Primary Examiner* — Samantha Shterengarts
(74) *Attorney, Agent, or Firm* — Alston & Bird LLP

(57) ABSTRACT

The present invention relates to a method for preparing methylated amines using carbon dioxide and to the use of the method for manufacturing vitamins, pharmaceutical products, glues, acrylic fibres and synthetic leathers, pesticides and fertilisers. The invention also relates to a method for manufacturing vitamins, pharmaceutical products, glues, acrylic fibres, synthetic leathers, pesticides and fertilisers, including a step of preparing methylated amines by the method according to the invention. The present invention also relates to a method for preparing marked methylated amines and to the uses thereof.

18 Claims, 1 Drawing Sheet

(56) References Cited

PUBLICATIONS

Shishigin E A et al.; *Russian Journal of General Chemistry*; vol. 75, No. 1; 2005; pp. 152.
Choudhry S C et al.; *Journal of Organic Chemistry*; 1989; vol. 54; pp. 3755-3757.
Ferguson J R et al., *J. Labelled Compd. Rad*; 2002; vol. 45; pp. 107-113.
Kikuchi T et al., *J. Labelled Compd. Rad.*; 2001; vol. 44; pp. 31-41.
Okamura T et al.; *J. Med. Chem.*; 2009; vol. 52; pp. 7284-7288.
Trefzer C et al.; *J. Am. Chem. Soc.*; 2010; vol. 132; pp. 13663-13665.

* cited by examiner

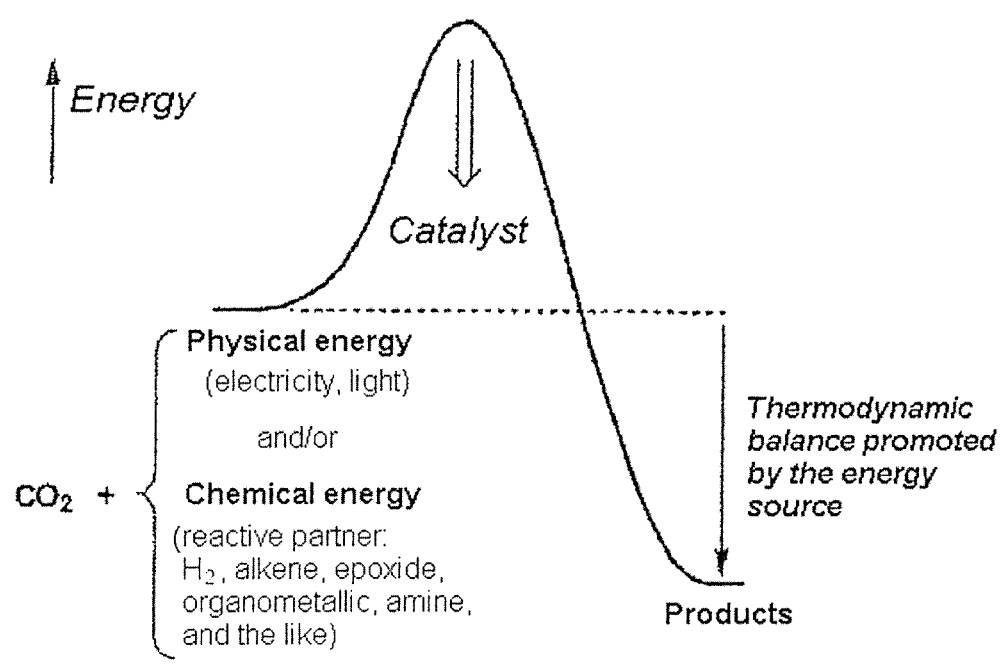

METHOD FOR PREPARING METHYLATED AMINES

FIELD

The present invention relates to a process for the preparation of methylated amines using carbon dioxide and the use of this process for the manufacture of vitamins, pharmaceutical products, adhesives, acrylic fibers, synthetic leather, pesticides and fertilizers.

It also relates to a process for the manufacture of vitamins, pharmaceutical products, adhesives, acrylic fibers, synthetic leather, pesticides and fertilizers comprising a stage of preparation of methylated amines by the process according to the invention.

The present invention additionally relates to a process for the preparation of labeled methylated amines and to their uses.

BACKGROUND

The use of $CO_2$ which can be recovered in value as carbon source for the production of chemical consumables is a key challenge in order to reduce its accumulation in the atmosphere but also in order to control our dependence on fossil fuels.

The greatest challenge faced by scientists and industrialists is to recycle $CO_2$, that is to say, to develop reactions which make it possible to produce chemical compounds, such as, for example, fuels, plastic polymers, medicaments, detergents, high tonnage molecules, conventionally obtained by petrochemical methods. The technical difficulty lies in the development of chemical reactions which make it possible to functionalize the $CO_2$ while reducing the central carbon atom (i.e., by replacing the C—O bonds of the $CO_2$ with C—H or C—C bonds).

In view of the high thermodynamic stability of carbon dioxide, its conversion into novel chemical consumables necessarily involves an external energy source so as to promote the thermodynamic balance of the chemical transformation represented in FIG. 1.

Today, all the efforts of the scientific community are focused on the use of electricity or light to carry out the electroreduction or photoreduction of the $CO_2$ to give formic acid, methanal, methanol and methane (Morris, A. J., Meyer, G. J. and Fujita, E., *Accounts Chem. Res.*, 2009, 42 1983). In fact, this field of research is the subject of intense international competition.

A recent paper describes that the use of silane compounds makes it possible to reduce $CO_2$ under organocatalytic conditions (Riduan, S. N., Zhang, Y. G. and Ying, J. Y., *Angewandte Chemie-International Edition*, 2009, 48, 3322). In this case, the silane compound is a reactive entity high in energy and the use of the catalyst promotes the kinetic balance. The authors describe the formation of silyl products of formyl (SiOCHO), acetal ($SiOCH_2OSi$) and methoxy ($SiOCH_3$) types. While this strategy is justified by the importance of the uses of the reduction products of $CO_2$ in the chemical industry (HCOOH, $H_2CO$, $CH_3OH$), it should nevertheless be noted that these molecules are currently used on a scale which remains very low with respect to the amount of available $CO_2$ which can be recovered in value. In other words, if these molecules were produced exclusively from $CO_2$, they would make it possible to recover in value, taking into account the current market, only 3.4% of the $CO_2$ produced each year which can be recovered in value (2.5 Gt/year) (Panorama des voies de valorisation du $CO_2$ [Overview of the routes for recovering $CO_2$ in value], ADEME, June 2010, http://www2.ademe.fr/servlet/getDoc?cid=96&m=3&id=72052 &p1=30&ref=12441).

Thus, it is necessary to try to diversify the nature and the number of chemical consumables which can be obtained from $CO_2$.

Another strategy for the conversion of $CO_2$ into novel chemical consumables consists in using a reactive (high in energy) chemical partner to promote the thermodynamic balance of the chemical transformation of $CO_2$. This strategy is also not very well represented on the scientific scene but it will make it possible, in the long run, to considerably open up the supply of molecules available from $CO_2$. The only industrial process based on this approach is the synthesis of urea obtained by condensation of ammonia with $CO_2$, as shown in equation 1 below (Sakakura, T., Choi, J. C. and Yasuda, H., *Chem. Rev.*, 2007, 107, 2365).

(equation 1)

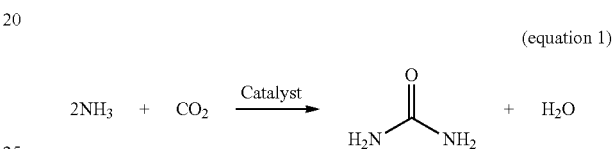

According to the same principle, the synthesis of polycarbonates by $CO_2$/epoxides copolymerization is in the process of industrialization as shown in equation 2 below (Panorama des voies de valorisation du $CO_2$ [Overview of the routes for recovering $CO_2$ in value], ADEME, June 2010, http://www2.ademe.fr/servlet/getDoc?cid=96&m=3&id=72052 &p1=30&ref=12441).

(equation 2)

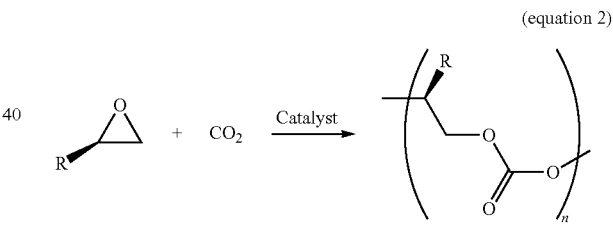

In both these syntheses (equations 1 and 2), there is no formal reduction of the central carbon atom of the $CO_2$.

Still with the aim of obtaining novel chemical consumables, it is possible to envisage converting the $CO_2$ into amine compounds and more specifically into methylated amines. Methylated amines (of general formula $R^1R^2NCH_3$) are a class of chemical compounds which are important in the chemical industry, where they are commonly used as solvents, reactants, fertilizers, herbicides, fungicides, active principles for medicaments and precursors of plastics (Amines: Synthesis, Properties and Applications, Lawrence, S. A., Cambridge University Press, 2006; Arpe, H.-J. and Hawkins, S., Industrial Organic Chemistry, Wiley-VCH, Weinheim, 1997; M. F. Ali; B. M. El Ali and J. G. Speight, Handbook of Industrial Chemistry—Organic Chemicals, McGraw-Hill, New York, 2005).

Methylated amines (of general formula $R^1R^2NCH_3$) are generally synthesized by reaction between an amine of general formula $R^1R^2NH$ and an electrophilic methylating agent, such as methyl iodide, methanol, dimethyl sulfate or dimethyl carbonate, preferably in the presence of a base.

Alternatively, methylated amines can be obtained by employing paraformaldehyde in the presence of a reducing agent ($H_2$, $NaBH_4$).

These different synthetic routes thus do not involve $CO_2$ as carbon source for the methylation of the N—H bond of the amine.

The synthesis of methylated amines from $CO_2$ is not very extensively described. It is in particular described by three publications:

In 1985, Ram and Ehrenkaufer described the carboxylation of amines in the presence of $CO_2$. After alkylation or silylation, the carbamic esters obtained are reduced with lithium aluminum hydride ($LiAlH_4$) (S. Ram and R. E. Ehrenkaufer, Tetrahedron Lett., 1985, Vol. 26, Issue 44, pp. 5367-5370).

According to a similar strategy, a three-stage method was developed by Jung et al.: the first stage consists in carrying out the carbonation of the amine in the presence of cesium carbonate. In a second stage, the carbamate thus formed is covalently grafted to a "Merrifield" resin. Finally, the carbamic ester supported on resin is reduced to methylated amine by reduction with lithium aluminum hydride ($LiAlH_4$) (R. N. Savatore, F. X. Chu, A. S. Nagle, E. A. Kapxhiu, R. M. Cross and K. W. Jung, Tetrahedron, 2002, Vol. 58, pp. 3329-3347).

A different strategy was developed by Ram and Spicer in 1989. It is based on the silylation of the N—H bond of an amine by hexamethyldisilazane ($Me_3SiSiMe_3$), followed by reaction with $CO_2$ in the presence of lithium aluminum hydride ($LiAlH_4$) (S. Ram and L. D. Spicer, Synthetic Communications, 1989, Vol. 19, pp. 3561-3571).

These synthetic routes exhibit disadvantages, in particular:
- the source of hydrides is $LiAlH_4$, a harsh reducing agent incompatible with the presence of functional groups on the amines;
- the processes involve several stages which require intermediate purifications;
- the reactions are not catalytic, which compels the use of powerful reactants (such as $LiAlH_4$) and the use of multiple stages for improving the yields and selectivities.

In the context of the synthesis of methylated amines using carbon dioxide, the technical challenge to be answered is that of combining the functionalization of the carbon dioxide (formation of a C—N bond) with a stage of chemical reduction (formation of three C—H bonds). In order to maximize the energy efficiency of such a transformation, it is necessary to develop reactions with a limited number of stages (ideally just one) and which are catalyzed, in order to prevent energy losses of a kinetic nature.

Labeled methylated amines, incorporating radioactive isotopes and/or stable isotopes, are moreover of particular interest in many fields, such as, for example, in life sciences (study/elucidation of enzymatic mechanisms or of biosynthetic mechanisms, in biochemistry and the like), environmental sciences (tracing of waste, and the like), research (study/elucidation of reaction mechanisms) or the research and development of novel pharmaceutical and therapeutic products. Thus, to develop a synthesis for the preparation of labeled methylated amines meeting the requirements indicated above meets a real need.

There thus exists a real need for a process for preparing methylated amines by the transformation of $CO_2$ which overcomes the disadvantages of the prior art, said process making it possible to combine the functionalization of the carbon dioxide with a stage of chemical reduction.

In particular, there exists a real need for a process which makes it possible to obtain, in just one step and with a good, indeed even excellent, selectivity, methylated amines from $CO_2$ and amines, under catalytic conditions and in the presence of a compound which provides for the reduction of $CO_2$ and which is compatible with the presence of functional groups on the amine.

In addition, there exists a real need to have available a process which makes it possible to obtain, in just one step and with an excellent selectivity, labeled methylated amines incorporating radioactive isotopes and/or stable isotopes starting from labeled reactants, such as, for example, labeled $CO_2$ and/or labeled amines, under catalytic conditions and in the presence of a compound which provides for the reduction of $CO_2$ and which is compatible with the presence of functional groups on the amine.

SUMMARY

It is a specific aim of the present invention to meet these needs by providing a process for the preparation of methylated amines of formula (I):

in which:
$R^1$ and $R^2$ represent, independently of one another, a hydrogen atom, an alkyl group, an alkenyl group, an alkynyl group, an aryl group, a heteroaryl group, a heterocycle, a silyl group, a siloxy group, an amino group, an aldimine of formula —N=CHR$^6$, or a ketimine of formula —N=CR$^6$R$^7$, said alkyl, alkenyl, alkynyl, aryl, heteroaryl, heterocycle, silyl, siloxy and amino groups optionally being substituted, or $R^1$ and $R^2$, taken together with the nitrogen atom to which they are bonded, form an optionally substituted heterocycle, or $R^1$ and $R^2$ form, with the nitrogen atom to which they are bonded, a carbon-nitrogen double bond (N=C) in order to result in an aldimine of formula —N=CHR$^6$ or in a ketimine of formula —N=CR$^6$R$^7$, and $R^6$ and $R^7$ represent, independently of one another, a hydrogen atom, an alkyl group, an alkenyl group, an alkynyl group, an aryl group, a heteroaryl group, a heterocycle, a silyl group, a siloxy group or an amino group, said alkyl, alkenyl, alkynyl, aryl, heteroaryl, heterocycle, silyl, siloxy and amino groups optionally being substituted, $R^1$, $R^2$, $R^6$ and $R^7$ optionally comprise an H, C, N, O, F, Si and/or S as defined below;

H represents a hydrogen atom ($^1$H), deuterium ($^2$H) or tritium ($^3$H);

C represents a carbon atom ($^{12}$C) or a $^{11}$C, $^{13}$C or $^{14}$C isotope;

N represents a nitrogen atom ($^{14}$N) or a $^{15}$N isotope;

O represents an oxygen atom ($^{16}$O) or an $^{18}$O isotope;

F represents a fluorine atom ($^{19}$F) or a $^{18}$F isotope;

Si represents a silicon atom ($^{28}$Si) or a $^{29}$Si or $^{30}$Si isotope;

S represents a sulfur atom ($^{32}S$) or a $^{33}S$, $^{34}S$ or $^{36}S$ isotope;

characterized in that an amine of formula (II), in which $R^1$ and $R^2$ and N are as defined above:

(II)

is reacted with $CO_2$, in which C and O are as defined above, in the presence of a catalyst and of a silane compound of formula (III):

(III)

in which:
H is as defined above,
$R^3$, $R^4$ and $R^5$ represent, independently of one another, a hydrogen atom, a halogen atom, a hydroxyl group, an alkyl group, an alkenyl group, an alkynyl group, an alkoxy group, a silyl group, a siloxy group, an aryl group or an amino group, said alkyl, alkenyl, alkynyl, alkoxy, silyl, siloxy, aryl and amino groups optionally being substituted, or
$R^5$ is as defined above and $R^3$ and $R^4$, taken together with the silicon atom to which they are bonded, form an optionally substituted silylated heterocycle.

The process of the invention has the advantage of making it possible to convert optionally labeled $CO_2$ into optionally labeled methylated amines with a large choice of optionally labeled amines of formula (II) (primary, secondary, aromatic, aliphatic, and the like, amines). In this process, said amines serve essentially to functionalize the $CO_2$ and the silane compounds of formula (III) provide for the reduction of $CO_2$, under catalytic conditions.

The methylated amines are thus obtained with a good yield (of the order of 35% to 100%, for example) and a good, indeed even excellent, selectivity (for example, more than 50%, indeed even more than 70%, of methylated amines isolated).

In the context of the present invention, the yield is calculated with respect to the amount of amine of formula (II) initially introduced, on the basis of the amount of methylated amine isolated:

Yield=$n$(methylated amine)/($n$(methylated amine)+$n$(amine)), n being the amount of material.

In the context of the present invention, the selectivity relates to the nature of the products formed from the amine of formula (II).

As indicated above, the process of the invention makes it possible to obtain the methylated amines of formula (I) in "just one step". In other words, in contrast to the processes of the state of the art in which the starting amines are subjected to successive chemical reactions with successive addition (one at a time) of the other reactants, with or without separation of the intermediate products, the process of the invention takes place in "just one step" during which all of the reactants (such as the bases, the silylated compounds, the reducing agents, in particular $LiAlH_4$, and the like) are found simultaneously in the reaction medium. Thus, industrially, the process of the invention is of great advantage as it makes it possible to gain in time, in production costs and in overall yield.

BRIEF DESCRIPTION OF THE DRAWINGS

FIG. 1 graphically illustrates the required energy for conversion of $CO_2$ inoto other products.

DETAILED DESCRIPTION

"Alkyl" is understood to mean, within the meaning of the present invention, an optionally substituted, saturated or unsaturated and linear, branched or cyclic carbon-based radical comprising from 1 to 12 carbon atoms. Mention may be made, as saturated and linear or branched alkyl, for example, of the methyl, ethyl, propyl, butyl, pentyl, hexyl, heptyl, octyl, nonyl, decyl, undecyl and dodecanyl radicals and their branched isomers. Mention may be made, as cyclic alkyl, of the cyclopropyl, cyclobutyl, cyclopentyl, cyclohexyl, bicyclo[2.1.1]hexyl and bicyclo[2.2.1]heptyl radicals. Mention may be made, as unsaturated cyclic alkyls, for example, of cyclopentenyl or cyclohexenyl. The unsaturated alkyls, also known as "alkenyl" or "alkynyl", respectively comprise at least one double bond or one triple bond. Mention may be made, as such, for example, of the ethenyl, propenyl, butenyl, pentenyl, hexenyl, acetylenyl, propynyl, butynyl, pentynyl and hexynyl radicals and their branched isomers. The alkyl group, within the meaning of the invention including the alkenyl and alkynyl groups, can optionally be substituted by one or more hydroxyl groups, one or more alkoxy groups, one or more halogen atoms chosen from the fluorine, chlorine, bromine and iodine atoms, one or more nitro (—$NO_2$) groups, one or more nitrile (—CN) groups, or one or more aryl groups, with the alkoxy and aryl groups as defined in the context of the present invention.

The term "aryl" denotes generally an aromatic cyclic substituent comprising from 6 to 20 carbon atoms. In the context of the invention, the aryl group can be mono- or polycyclic. Mention may be made, by way of indication, of the phenyl, benzyl and naphthyl groups. The aryl group can optionally be substituted by one or more hydroxyl groups, one or more alkoxy groups, one or more halogen atoms chosen from the fluorine, chlorine, bromine and iodine atoms, one or more nitro (—$NO_2$) groups, one or more nitrile (—CN) groups, one or more alkyl groups, or one or more aryl groups, with the alkoxy, alkyl and aryl groups as defined in the context of the present invention.

The term "heteroaryl" denotes generally an aromatic mono- or polycyclic substituent comprising from 5 to 10 members, including at least 2 carbon atoms, and at least one heteroatom chosen from nitrogen, oxygen or sulfur. Mention may be made, by way of indication, of the furyl, benzofuranyl, pyrrolyl, indolyl, isoindolyl, azaindolyl, thiophenyl, benzothiophenyl, pyridyl, quinolinyl, isoquinolyl, imidazolyl, benzimidazolyl, triazolyl, pyrazolyl, oxazolyl, isoxazolyl, benzoxazolyl, thiazolyl, benzothiazolyl, isothiazolyl, pyridazinyl, pyrimidilyl, pyrimidinyl, pyrazinyl, triazinyl, cinnolinyl, phthalazinyl, quinazolinyl, 1,1-diphenylhydrazinyl and 1,2-diphenylhydrazinyl groups. The heteroaryl group can optionally be substituted by one or more hydroxyl groups, one or more alkoxy groups, one or more halogen atoms chosen from the fluorine, chlorine, bromine and iodine atoms, one or more nitro (—$NO_2$) groups, one or more nitrile (—CN) groups, one or more aryl groups, or one or more alkyl groups, with the alkyl, alkoxy and aryl groups as defined in the context of the present invention.

The term "alkoxy" means an alkyl group, as defined above, bonded via an oxygen atom (—O-alkyl).

The term "heterocycle" denotes generally a saturated or unsaturated and mono- or polycyclic substituent comprising from 5 to 10 members and comprising from 1 to 4 heteroatoms chosen, independently of one another, from nitrogen, oxygen and sulfur. Mention may be made, by way of indication, of the morpholinyl, piperidinyl, piperazinyl, pyrrolidinyl, imidazolyl, imidazolidinyl, imidazolinyl, pyrazolidinyl, tetrahydrofuranyl, tetrahydropyranyl, tetrahydropyrimidinyl, triazolyl, pyrazolyl, thianyl, oxazolidinyl, isoxazolidinyl, thiazolidinyl and isothiazolidinyl substituents. The heterocycle can optionally be substituted by one or more hydroxyl groups, one or more alkoxy groups, one or more aryl groups, one or more halogen atoms chosen from the fluorine, chlorine, bromine and iodine atoms, one or more nitro (—NO$_2$) groups, one or more nitrile (—CN) groups, or one or more alkyl groups, with the alkyl, alkoxy and aryl groups as defined in the context of the present invention.

Halogen atom is understood to mean an atom chosen from the fluorine, chlorine, bromine or iodine atoms.

"Silyl" group is understood to mean a group of formula [—Si(X)$_3$] in which each X, independently of one another, is chosen from a hydrogen atom, one or more halogen atoms chosen from the fluorine, chlorine, bromine or iodine atoms, one or more alkyl groups, one or more alkoxy groups, one or more aryl groups, or one or more siloxy groups, with the alkyl, alkoxy, aryl and siloxy groups as defined in the context of the present invention. When at least one of the X symbols represents several siloxy groups, said siloxy groups can be repeated several times so as to result in polymeric organosilanes of general formula:

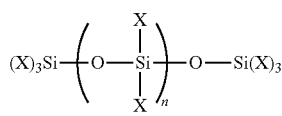

in which X is as defined above and n is an integer of between 1 and 20 000, advantageously between 1000 and 5000. Mention may be made, as such, for example, of polydimethylsiloxane (PDMS) or polymethylhydrosiloxane (PMHS).

"Siloxy" group is understood to mean a silyl group as defined above bonded via an oxygen atom (—O—Si(X)$_3$).

Within the meaning of the invention, "silylated heterocycle" is understood to mean a saturated or unsaturated and mono- or polycyclic substituent comprising from 5 to 15 members and comprising at least one silicon atom and optionally at least one other heteroatom chosen from nitrogen, oxygen or sulfur. Said silylated heterocycle can optionally be substituted by one or more hydroxyl groups, one or more alkyl groups, one or more alkoxy groups, one or more halogen atoms chosen from the fluorine, chlorine, bromine and iodine atoms or one or more aryl groups with the alkyl, alkoxy and aryl groups as defined in the context of the present invention. Mention may be made, among silylated heterocycles, for example, of 1-silacyclo-3-pentene or 1-methyl-1-hydrido-2,3,4,5-tetraphenyl-1-silacyclo-pentadiene, according to the formulae below.

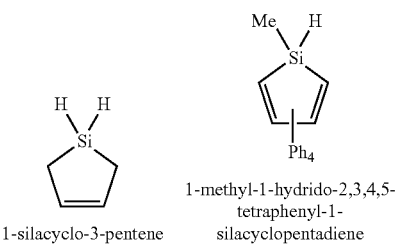

1-silacyclo-3-pentene 1-methyl-1-hydrido-2,3,4,5-tetraphenyl-1-silacyclopentadiene Mention may also be made, for example, of methylsiloxane, 1-phenyl-1-silacyclohexane, 1-sila-bicyclo[2.2.1]heptane, 1-methyl-1-silacyclopentane and 9,9-dihydro-9-silafluorene, corresponding to the formulae below.

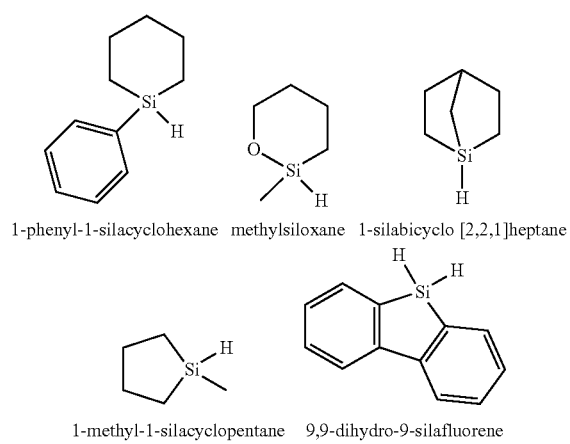

1-phenyl-1-silacyclohexane   methylsiloxane   1-silabicyclo [2,2,1]heptane 1-methyl-1-silacyclopentane   9,9-dihydro-9-silafluorene The silylated heterocycles of the invention can be available commercially or can, if appropriate, be prepared by known synthetic processes, such as, for example, described by C. L. Smith et al., *Journal of Organometallic Chemistry*, 81 (1974), pp. 33-40; G. D. Homer, *Journal of the American Chemical Society*, 95, 23, (1973), pp. 7700-7707; L. Spialter et al., *Journal of the American Chemical Society*, 93, 22 (1971), pp. 5682-5686; R. West, *Journal of the American Chemical Society* (1954), pp. 6015-6017. A person skilled in the art will be in a position to employ and adapt the known processes to the synthesis of the various silylated heterocycles.

"Amino" group is understood to mean a group of formula —NR$^6$R$^7$ in which:

R$^6$ and R$^7$ represent, independently of one another, a hydrogen atom, an alkyl group, an alkenyl group, an alkynyl group, an aryl group, a heteroaryl group, a heterocycle, a silyl group or a siloxy group, with the alkyl, alkenyl, alkynyl, aryl, heteroaryl, heterocycle, silyl and siloxy groups as defined in the context of the present invention; or R$^6$ and R$^7$, taken together with the nitrogen atom to which they are bonded, form a heterocycle optionally substituted by one or more hydroxyl groups, one or more alkyl groups, one or more alkoxy groups, one or more halogen atoms chosen from the fluorine, chlorine, bromine and iodine atoms, one or more nitro (—NO$_2$) groups, one or more nitrile (—CN) groups, or one or more aryl groups, with the alkyl, alkoxy and aryl groups as defined in the context of the present invention.

When R$^1$ and R$^2$ form, with the nitrogen atom to which they are bonded, a carbon-nitrogen double bond (N═C) in order to result in an aldimine of formula —N=CHR⁶ or in a ketimine of formula —N=CR⁶R⁷ and when R⁶ and R⁷ represent, independently of one another, an alkyl group, an alkenyl group, an alkynyl group, an aryl group, a heteroaryl group, a heterocycle, a silyl group, a siloxy group or an amino group, said alkyl, alkenyl, alkynyl, aryl, heteroaryl, heterocycle, silyl, siloxy and amino groups as defined in the context of the present invention can optionally be substituted by one or more hydroxyl groups, one or more alkoxy groups, one or more aryl groups, one or more halogen atoms chosen from the fluorine, chlorine, bromine and iodine atoms, one or more nitro (—NO₂) groups, one or more nitrile (—CN) groups or one or more alkyl groups, with the alkyl, alkoxy and aryl groups as defined in the context of the present invention.

The substituents, radicals and groups defined above can optionally comprise deuterium (²H), tritium (³H), ¹¹C, ¹³C, ¹⁴C, ¹⁵N, ¹⁸O ¹⁸F, ²⁹Si, ³⁰Si, ³³S, ³⁴S or ³⁶S.

When the compounds of formulae (I), (II) and (III) comprise at least one radioactive label/radioactive tracer or one isotope, they can also be denoted by the formulae (I'), (II') and (III').

According to a preferred alternative form of the invention, in the amine of formula (II), R¹ and R² represent, independently of one another, a hydrogen atom, an alkyl group, an aryl group or a heteroaryl group, said alkyl, aryl and heteroaryl groups optionally being substituted, or R¹ and R², taken together with the nitrogen atom to which they are bonded, form an optionally substituted heterocycle.

Preferably, in the amine of formula (II), R¹ and R² represent, independently of one another, a hydrogen atom; an alkyl group chosen from methyl, ethyl, propyl, butyl, pentyl, hexyl or heptyl groups or their branched isomers or the cyclohexyl groups; an aryl group chosen from the benzyl or phenyl; or a heteroaryl group chosen from imidazolyl or benzimidazolyl; or R¹ and R², taken together with the nitrogen atom to which they are bonded, form a 5- to 6-membered heterocycle chosen from morpholine, piperidine, piperazine, pyrrolidine, oxazolidine, isoxazolidine, imidazole, in particular 1H-imidazole, tetrahydropyrimidine, in particular 1,4,5,6-tetrahydropyrimidine, triazole or pyrazole.

According to another preferred alternative form of the invention, in the silane compound of formula (III), R³, R⁴ and R⁵ represent, independently of one another, a hydrogen atom, an alkyl group, an alkoxy group, an aryl group, a silyl group or a siloxy group, said alkyl, alkoxy, silyl, siloxy and aryl groups optionally being substituted.

Preferably, in the silane compound of formula (III), R³, R⁴ and R⁵ represent, independently of one another:
 a hydrogen atom;
 an alkyl group chosen from methyl, ethyl, propyl, butyl, pentyl, hexyl or heptyl groups or their branched isomers;
 an alkoxy group, the alkyl group of which is chosen from the methyl, ethyl, propyl, butyl, pentyl, hexyl or heptyl groups or their branched isomers;
 an aryl group chosen from the benzyl or phenyl groups;
 a siloxy group;
 a silyl group of formula [—Si(X)₃] in which each X symbol, independently of one another, is chosen from a hydrogen atom, one or more halogen atoms chosen from the chlorine, bromine or iodine atoms, one or more alkyl groups chosen from the methyl, ethyl, propyl, butyl, pentyl, hexyl or heptyl groups or their branched isomers, one or more alkoxy groups, the alkyl group of which is chosen from the methyl, ethyl, propyl, butyl, pentyl, hexyl or heptyl groups or their branched isomers, one or more siloxy groups, the —Si(X)₃ group of which is as described in this embodiment, several siloxy groups which reoccur several times resulting in polymeric organosilanes of general formula:

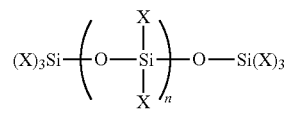

in which X is as defined in this embodiment and n is an integer of between 1 and 20 000, advantageously between 1000 and 5000.

Catalyst, within the meaning of the invention, is understood to mean any compound which is capable of modifying, in particular by increasing, the rate of the chemical reaction in which it participates and which is regenerated at the end of the reaction. This definition encompasses both catalysts, that is to say compounds which exert their catalytic activity without having to be subjected to any modification or conversion, and compounds (also known as precatalysts) which are introduced into the reaction medium and which are converted therein into a catalyst.

The catalysts can be chosen from organic catalysts or metal catalysts, the metal catalysts being chosen from metal salts or metal complexes. Organic catalysts exhibit the advantage of making it possible to escape the problems of toxicity generally observed for metal catalysts and also the problems of costs associated with the use of precious metals. In the process of the invention, the catalyst is preferably organic.

The organic catalysts are generally organic bases chosen from:
 nitrogenous bases, such as, for example, secondary or tertiary amines chosen from triazabicyclodecene (TBD), N-methyltriazabicyclodecene (MeTBD), 1,8-diazabicyclo[5.4.0]undec-7-ene (DBU), trimethylamine, triethylamine, piperidine, 4-dimethylaminopyridine (DMAP), 1,4-diazabicyclo[2.2.2]octane (DABCO), proline, phenylalanine, a thiazolium salt or N-diisopropylethylamine (DIPEA or DIEA);
 phosphorus-based bases, such as, for example, alkyl- and arylphosphines chosen from triphenylphosphine, 2,2'-bis(diphenylphosphino)-1,1'-binaphthyl (BINAP) or triisopropylphosphine; alkyl- and arylphosphonates chosen from diphenyl phosphate, triphenyl phosphate (TPP), tri(isopropylphenyl) phosphate (TIPP), cresyl diphenyl phosphate (CDP) or tricresyl phosphate (TCP); or alkyl and aryl phosphates chosen from di(n-butyl) phosphate (DBP), tris(2-ethylhexyl) phosphate or triethyl phosphate;
 carbon-based bases for which the protonation takes place on a carbon atom, such as, for example, an N-heterocyclic carbene, such as a carbene resulting from an imidazolium salt chosen from 1,3-bis(2,6-diisopropylphenyl)-1H-imidazol-3-ium (carbene A), 1,3-bis(2,6-diisopropylphenyl)-4,5-dihydro-1H-imidazol-3-ium (carbene C), 1,3-bis(2,4,6-trimethylphenyl)-1H-imidazol-3-ium (carbene B), 1,3-bis(2,4,6-trimethylphenyl)-4,5-dihydro-1H-imidazol-3-ium (carbene D), 4,5-dichloro-1,3-bis(2,6-diisopropylphenyl)-1H-imidazol-3-ium (carbene E), 1,3-di(tert-butyl)-1H-imidazol-3-ium (carbene F) or 1,3-di(tert-butyl)-4,5-dihydro-1H-imidazol-3-ium salts, said salts being, for example, in the form of chloride salts, as represented below:

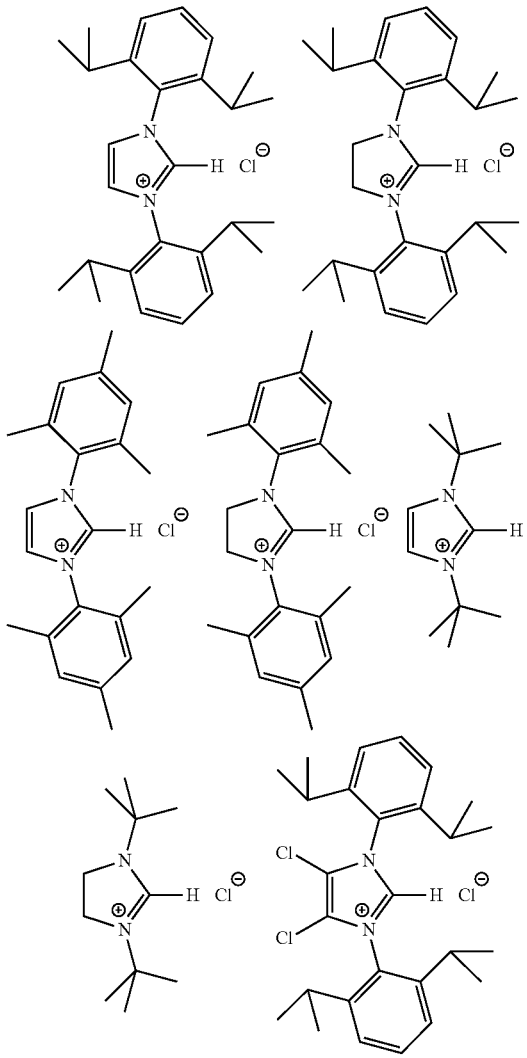

or
oxygen-based bases, such as, for example, hydrogen peroxide, benzoyl peroxide or alkoxide chosen from sodium or potassium methoxide, ethoxide, propoxide, butoxide, pentoxide or hexoxide.

The organic catalyst is advantageously:
a secondary or tertiary amine chosen from triazabicyclodecene (TED), N-methyltriazabicyclodecene (MeTBD), 1,8-diazabicyclo[5.4.0]undec-7-ene (DBU), trimethylamine, triethylamine, piperidine, 4-dimethylaminopyridine (DMAP), 1,4-diazabicyclo[2.2.2]octane (DABCO), proline, phenylalanine, a thiazolium salt or N-diisopropylethylamine (DIPEA or DIEA), or
an N-heterocyclic carbene, such as a carbene resulting from an imidazolium salt chosen from 1,3-bis(2,6-diisopropylphenyl)-1H-imidazol-3-ium (carbene A), 1,3-bis(2,6-diisopropylphenyl)-4,5-dihydro-1H-imidazol-3-ium (carbene C), 1,3-bis(2,4,6trimethylphenyl)-1H-imidazol-3-ium (carbene B), 1,3-bis(2,4,6-trimethylphenyl)-4,5-dihydro-1H-imidazol-3-ium (carbene D), 4,5-dichloro-1,3-bis(2,6-diisopropylphenyl)-1H-imidazol-3-ium (carbene E), 1,3-di(tert-butyl)-1H-imidazol-3-ium (carbene F) or 1,3-di(tert-butyl)-4,5-dihydro-1H-imidazol-3-ium salts, said salts being, for example, in the form of chloride salts, as represented below:

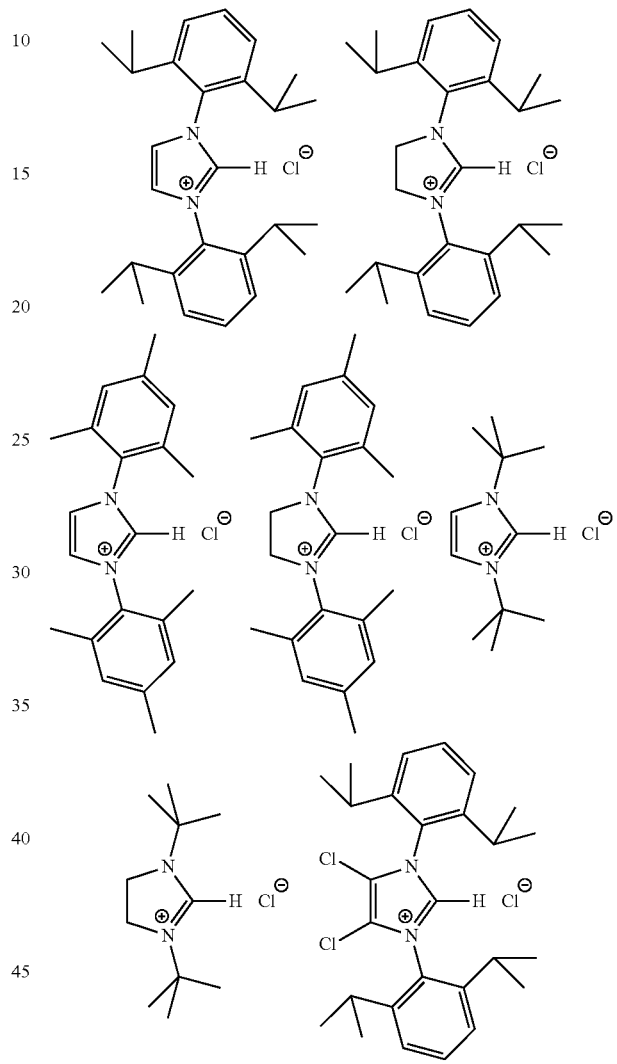

According to a preferred alternative form of the invention, the organic catalyst is chosen from triazabicyclodecene (TBD), N-methyltriazabicyclodecene (MeTBD), 1,8-diazabicyclo[5.4.0]undec-7-ene (DBU), or an N-heterocyclic carbene, such as a carbene resulting from an imidazolium salt, such as 1,3-bis(2,6-diisopropylphenyl)-1H-imidazol-3-ium chloride (carbene A), 1,3-bis(2,6-diisopropylphenyl)-4,5-dihydro-1H-imidazol-3-ium chloride (carbene C), 1,3-di(tert-butyl)-1H-imidazol-3-ium chloride, 1,3-di(tert-butyl)-4,5-dihydro-1H-imidazol-3-ium chloride (carbene F), 1,3-bis(2,4,6-trimethylphenyl)-1H-imidazol-3-ium chloride (carbene B), 1,3-bis(2,4,6-trimethylphenyl)-4,5-dihydro-1H-imidazol-3-ium chloride (carbene D) or 4,5-dichloro-1,3-bis(2,6-diisopropylphenyl)-1H-imidazol-3-ium chloride (carbene E).

When the catalyst is a metal catalyst, it can be chosen from the salts or complexes of:
- metals chosen from boron, silicon, aluminum, gallium, tin or indium;
- alkali metals chosen from sodium or potassium;
- alkaline earth metals chosen from magnesium or calcium;
- transition metals chosen from nickel, iron, cobalt, zinc, copper, rhodium, ruthenium, platinum, palladium or iridium;
- rare earth metals chosen from lanthanum, cerium, praseodymium or neodymium.

By way of examples, the metal catalyst can be chosen from the following salts or complexes:
- $Al(OiPr)_3$, $SnCl_2$ or $InBr_3$, as metal salts or complexes;
- $Na_2CO_3$, $K_2CO_3$ or $Cs_2CO_3$, as salts or complexes of alkali metals;
- $MgSO_4$ or $Ca(BH_4)_2$, as salts or complexes of alkaline earth metals;
- $Fe(BH_4)_2 \cdot 6H_2O$, $Fe(BF_4)_2 \cdot 6H_2O$, $Fe(acac)_3$, CuCl, $Cu(OAc)_2(H_2O)$, $Zn(OAc)_2$, Zn(BDI)Et, $ZnEt_2$, $ZnCl_2$ or $ZnSO_4$, as salts or complexes of transition metals;
- $La(OTf)_3$ or $CeCl_3$, as salts or complexes of rare earth metals.

Metal complex is understood to mean an organometallic or inorganic coordination compound in which a metal ion is bonded to an organic or inorganic ligand. An organometallic or inorganic complex can be obtained by mixing a metal salt with a ligand, the latter bonding to the metal via phosphorus, carbon, nitrogen, oxygen, hydrogen or silicon atoms, for example. Mention may be made, as organic or inorganic ligand and by way of indication, of a ligand of the phosphine or amine type, such as, for example, tris[2-(diphenylphosphino)ethyl]phosphine ($PP_3$), carbene A, tricyclohexylphosphine, acetate (AcO), acetylacetonate (acac), 1,2-bis(diphenylphosphino)ethane (dppe), N,N,N',N'-tetramethylethylenediamine (TMEDA), N,N'-bis(2,6-diisopropylphenyl)-β-diketiminate (BDI), 1,2-bis(diphenylphosphino)benzene (dppb) or pyridine.

According to a preferred alternative form of the invention, the metal catalyst is obtained:
- by mixing an iron metal salt, such as, for example, $Fe(acac)_3$, $Fe(acac)_2$ or $Fe(BF_4)_2 \cdot 6H_2O$, with a ligand of phosphine or amine type, such as, for example TMEDA, dppe or $PP_3$; or else
- by mixing a zinc salt, such as, for example, Zn(BDI)Et, $Zn(OAc)_2$ or $ZnEt_2$, with a ligand of amine type, such as, for example, TMEDA, pyridine or carbene A.

Some of the abbreviations used for the ligands are represented below:

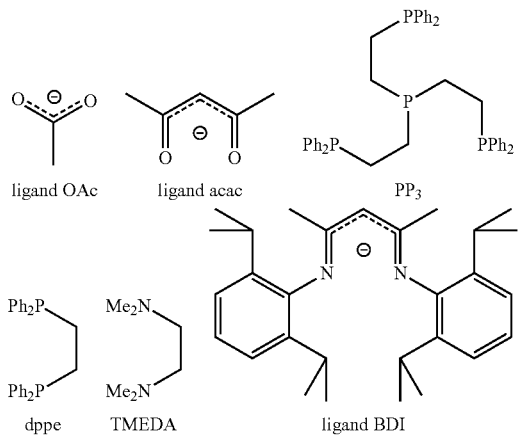

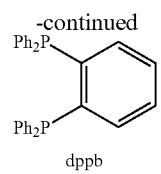

Without wishing to be committed by theory, the amine $R^1R^2NH$ serves to functionalize the $CO_2$ by the formation of intermediates of carbamate type and the silane provides the stage of reduction of said intermediates of carbamate type.

The catalysts can, if appropriate, be immobilized on heterogeneous supports in order to ensure ready separation of said catalyst and/or the recycling thereof. Said heterogeneous supports can be chosen from supports based on silica gel or on plastic polymers, such as, for example, polystyrene, carbon-based supports chosen from carbon nanotubes, silicon carbide, alumina or magnesium chloride ($MgCl_2$).

In the process according to the invention, the reaction can be carried out under a $CO_2$ pressure by sparging $CO_2$ into the reaction medium or under a dry atmosphere comprising $CO_2$ (dried ambient air comprising, for example, approximately 78% by volume of nitrogen, 21% by volume of oxygen and approximately from 0.2% to 0.04% by volume of carbon dioxide). The reaction can also be carried out using supercritical $CO_2$.

Preferably, the reaction is carried out under a $CO_2$ pressure.

The pressure of the $CO_2$ can then be between 1 and 50 bar, preferably between 1 and 30 bar and more preferably between 1 and 10 bar, limits included.

The temperature of the reaction can be between 25 and 150° C., preferably between 50 and 125° C. and more preferably between 70 and 100° C., limits included.

The duration of the reaction depends on the degree of conversion of the amine of formula (II). The reaction is advantageously maintained until complete conversion of the amine in the formula (II). The reaction can be carried out for a period of time of 5 minutes to 72 hours, advantageously of 15 minutes to 48 hours and preferably of 1 to 48 hours, limits included.

The process of the invention, in particular the reaction between the different reactants, can take place in a or a mixture of at least two solvent(s) chosen from:
- ethers, preferably diethyl ether or THF;
- hydrocarbons, preferably benzene or toluene;
- nitrogenous solvents, preferably pyridine or acetonitrile;
- sulfoxides, preferably dimethyl sulfoxide;
- alkyl halides, preferably chloroform or methylene chloride.

According to a preferred alternative form of the invention, it is not necessary to add an additional solvent. In this case, the amine of formula (II) is the solvent. Thus, in addition to its role of functionalizing the $CO_2$, the amine serves as solvent.

The molar ratio of the silane compound of formula (III) to the amine of formula (II) is from 1 to 10 and preferably from 1 to 3, limits included.

The amount of catalyst is from 0.001 to 1 molar equivalent, preferably from 0.001 to 0.9 molar equivalent, more preferably from 0.01 to 0.9 molar equivalent and more preferably still from 0.01 to 0.5 molar equivalent, limits included, with respect to the amine of formula (II).

The different reactants used in the process of the invention (the amines of formula (II), the silane compounds of formula (III), the (pre)catalysts, and the like) are generally commercial compounds or can be prepared by any process known to a person skilled in the art.

The invention also relates to the process for the preparation of labeled methylated amines of formula (I'):

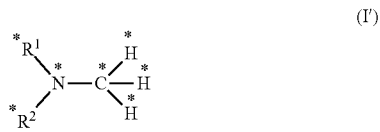

in which:
R$^1$*, R$^2$*, R$^6$* and R$^7$* are as defined above and optionally comprise an H*, C*, N*, O*, F*, Si* and/or S* as defined below;
H* represents a hydrogen atom ($^1$H), deuterium ($^2$H) or tritium ($^3$H);
C* represents a carbon atom ($^{12}$C) or a $^{11}$C, $^{13}$C or $^{14}$C isotope;
N* represents a nitrogen atom ($^{14}$N) or a $^{15}$N isotope;
O* represents an oxygen atom ($^{16}$O) or an $^{18}$O isotope;
F* represents a fluorine atom ($^{19}$F) or a $^{18}$F isotope;
Si* represents a silicon atom ($^{28}$Si) or a $^{29}$Si or $^{30}$Si isotope;
S* represents a sulfur atom ($^{32}$S) or a $^{33}$S, $^{34}$S or $^{36}$S isotope;
characterized in that an amine of formula (II'), in which R$^1$*, R$^2$* and N* are as defined above:

is reacted with CO*$_2$, in which C* and O* are as defined above, in the presence of a catalyst and of a silane compound of formula (III'):

in which:
R$^3$, R$^4$, R$^5$ and H* are as defined above.

The compounds of formula (I') correspond in fact to the compounds of formula (I) comprising at least one chosen radioactive label/radioactive tracer or one chosen isotope.

Isotopes are understood to mean, for one and the same element, two atoms having the same number of protons (and of electrons) but a different number of neutrons. As they have the same number of electrons and protons, the chemical properties of isotopes of one and the same element and are virtually identical. However, there may exist slight variations in the rate of a chemical reaction when one of the atoms of a reactant is replaced by one of its isotopes. On the other hand, as the nucleus does not comprise the same number of neutrons, the mass of the atoms varies, which may render the atom unstable: this is why they may be radioactive. They are then radioactive isotopes. In the context of the invention, the term "isotopes" may also encompass "radioactive isotopes".

Radioactive labeling is the fact of combining, with a given molecule or a given compound, an isotope which will make it possible to monitor the change and/or the fixing of the molecules, for example, in an organ. The radioactive tracer is the radioactive element(s) present within a molecule for monitoring the course of this substance, for example, in an organ.

This process can thus make it possible to access methylated amines labeled with $^{11}$C, $^{13}$C, $^{14}$C, $^{15}$N, $^2$H (D) and/or $^3$H (T).

The use of molecules for tracing, metabolism, imaging, and the like purposes is described in detail in the literature (U. Pleiss and R. Voges, "Synthesis and Applications of Isotopically Labelled Compounds", Volume 7, Wiley-VCH, 2001; R. Voges, J. R. Heys and T. Moenius, "Preparation of Compounds Labeled with Tritium and Carbon-14", Wiley-VCH, Chippenham (UK), 2009). The possibility of forming labeled methylated amines can be provided by the availability of the corresponding labeled reactants, for example by:
the amines R$^1$R$^2$NH enriched in $^{15}$N are accessible from ammonium chloride enriched in $^{15}$N: [$^{15}$NH$_4$][Cl] (Yong-Joo Kim, Max P. Bernstein, Angela S. Galiano Roth, Floyd E. Romesberg, Paul G. Williard, David J. Fuller, Aidan T. Harrison and David B. Collum, J. Org. Chem., 1991, 56, pp. 4435-4439);
amines R$^1$R$^2$NH$_2$ with R$^1$ and/or R$^2$ labeled are prepared by the synthetic routes described in detail by U. Pleiss and R. Voges, "Synthesis and Applications of Isotopically Labelled Compounds", Volume 7, Wiley-VCH, 2001; and R. Voges, J. R. Heys and T. Moenius, "Preparation of Compounds Labeled with Tritium and Carbon-14", Wiley-VCH, Chippenham (UK), 2009;
CO$_2$ labeled with $^{11}$C or $^{14}$C is the main source of $^{11}$C and $^{14}$C is obtained by acidification of labeled barium carbonate Ba$^{14}$CO$_3$ (R. Voges, J. R. Heys and T. Moenius, "Preparation of Compounds Labeled with Tritium and Carbon-14", Wiley-VCH, Chippenham (UK), 2009);
silanes R$^3$R$^4$R$^5$Si—H labeled with $^2$H (deuterium or D) or $^3$H (tritium or T) are accessible from the corresponding chlorosilane R$^3$R$^4$R$^5$Si—Cl and lithium hydride (LiH) or lithium aluminum hydride (LiAlH$_4$), the hydrides both being available in deuterated and tritiated versions (T. A. Kochina, D. V. Vrazhnov, E. N. Sinotova, V. V. Avrorin, M. Yu. Katsap and Yu. V. Mykhov, Russian Journal of General Chemistry, Vol. 72, No. 8, 2002, pp. 1222-1224; E. A. Shishigin, V. V. Avrorin, T. A. Kochina and E. N. Sinotova, Russian Journal of General Chemistry, Vol. 75, No. 1, 2005, pp. 152).

Preferably, CO$_2$ labeled with $^{11}$C or $^{14}$C is used in the process for the preparation of labeled methylated amines of formula (I').

Molecules labeled with $^{14}$C have contributed to many advances in life sciences (enzymatic mechanisms, biosynthetic mechanisms, biochemistry), environmental sciences (tracing of waste), research (elucidation of reaction mechanisms) or diagnosis, or research and development of novel pharmaceutical and therapeutic products. This is because molecules labeled with $^{14}$C exhibit an advantage in metabolical studies and $^{14}$C is easily detectable and quantifiable in both an in vitro environment and in vivo.

The main source of $^{14}$C is $^{14}$CO$_2$, which is obtained by acidification of barium carbonate Ba$^{14}$CO$_3$. The development of processes for the synthesis of base molecules used in the preparation of medicaments is thus essential in order to produce active principles labeled with $^{14}C$, the metabolism of which can thus be determined (R. Voges, J. R. Heys and T. Moenius, "Preparation of Compounds Labeled with Tritium and Carbon-14", Wiley-VCH, Chippenham (UK), 2009).

The major constraint limiting the synthesis of molecules labeled with $^{14}C$ is the need to have a high yield of $^{14}C$ product formed with respect to the amount of $^{14}CO_2$ used and to be based on a restricted number of stages in order to limit as much as possible the costs related to the use of $Ba^{14}CO_3$ (U. Pleiss and R. Voges, "Synthesis and Applications of Isotopically Labelled Compounds", Volume 7, Wiley-VCH, 2001; R. Voges, J. R. Heys and T. Moenius, "Preparation of Compounds Labeled with Tritium and Carbon-14", Wiley-VCH, Chippenham (UK), 2009).

The process according to the invention meets these requirements as the $CO_2$ operating pressure can be low, for example from 0.2 to 1 bar. In addition, the degree of incorporation of $CO_2$ (or yield with respect to the $CO_2$ introduced) remains high and can, for example, exceed 95%.

The conditions of temperature, of reaction time and of solvent and also the amounts of reactants and catalysts employed in the process for the preparation of labeled methylated amines of formula (I') are those described above in the context of the process for the preparation of methylated amines of formula (I).

Finally, the synthesis of methylated amines labeled with $^{14}C$ according to the present invention is a very marked improvement in comparison with the known technologies generally based on a minimum of three stages, in which the $CO_2$ is first reduced to give methanol in order to be subsequently converted into methyl iodide. The latter is subsequently used as methylating reagent and reacted with an amine in order to form the methylated amine (S. C. Choudhry, L. Serico and J. Cupano, Journal of Organic Chemistry, 1989, Vol. 54, pp. 3755-3757).

The process of the invention can thus make it possible to access methylated amines in just one step starting with $CO_2$ with good yields and a good selectivity. The advantage of methylated amines labeled with $^{14}C$ in the synthesis of complex molecules labeled with $^{14}C$ is illustrated in the following references, in the case of pharmaceutical active principles: J. R. Ferguson, S. J. Hollis, G. A. Johnston, K. W. Lumbard and A. V. Stachulski, J. Labelled Compd. Rad. 2002, Vol. 45, pp. 107-113; T. Kikuchi, K. Fukushi, N. Ikota, T. Ueda, S. Nagatsuka, Y. Arano and T. Irie, J. Labelled Compd. Rad. 2001, Vol. 44, pp. 31-41; T. Okamura, T. Kikuchi, K. Fukushi and T. Irie, J. Med. Chem. 2009, Vol. 52, pp. 7284-7288; C. Trefzer, M. Rengifo-Gonzalez, M. J. Hinner, P. Schneider, V. Makarov, S. T. Cole and K. Johnsson, J. Am. Chem. Soc. 2010, Vol. 132, pp. 13663-13665.

Another subject matter of the invention is the use of the process for the preparation of methylated amines of formula (I) according to the invention in the manufacture of vitamins, pharmaceutical products, adhesives, acrylic fibers, synthetic leather, pesticides and fertilizers.

Another subject matter of the invention is the use of the process for the preparation of methylated amines of formula (I') according to the invention in the manufacture of radioactive tracers and radioactive labels. Mention may be made, as examples of radioactive tracers and radioactive labels, of 6-bromo-7-[$^{11}C$] and 6-bromo-7-[$^{14}C$] and [N-[$^{14}C$]methyl]-2-(4'-(methylamino)phenyl)-6-hydroxybenzothiazole (also known as [$^{14}C$] PIB), the structures of which are represented below:

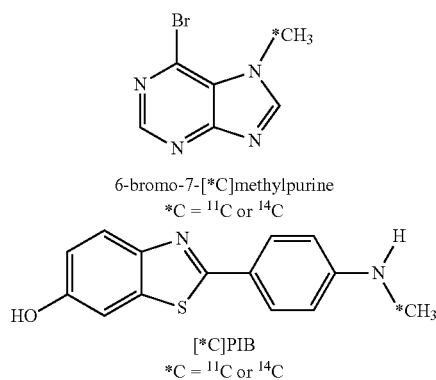

6-bromo-7-[*C]methylpurine
*C = $^{11}C$ or $^{14}C$

[*C]PIB
*C = $^{11}C$ or $^{14}C$

An additional subject matter of the invention is a process for the manufacture of vitamins, pharmaceutical products, adhesives, acrylic fibers, synthetic leather, pesticides and fertilizers, characterized in that it comprises a step of preparation of methylated amines of formula (I) by the process according to the invention.

An additional subject matter of the invention is a process for the manufacture of tracers and radioactive tracers, characterized in that it comprises a step of preparation of methylated amines of formula (I') by the process according to the invention.

As already indicated, the process according to the invention results in the formation of methylated amines with a good yield (of the order of 35% to 100%, for example) and a good, indeed even excellent, selectivity (for example, more than 50%, indeed even more than 70%, of methylated amines isolated). A simple filtration can make it possible to recover the optionally supported catalyst and to remove the possible silylated by-products formed.

Whether for the preparation of methylated amines of formula (I) or of the labeled methylated amines of formula (I'), in addition to the good yield and very good selectivity, the process of the invention makes it possible to obtain said methylated amines in just one step and to use:
    $CO_2$ as carbon source, and
    a mild reducing agent (the silane of formula (III) or (III')), compatible with the optional presence of functional groups on the amine.

Other advantages and characteristics of the present invention will become apparent on reading the examples below, given by way of illustration and without implied limitation, and the appended FIG. 1, which represents the thermodynamic stability of carbon dioxide and the need to resort to an external energy source to promote the thermodynamic balance of the chemical transformation and the conversion of $CO_2$ to

EXAMPLES

Example 1

The process for the preparation of methylated amines of formula (I) can be carried out according to the following experimental protocol.

The reactants used, in particular the amine $R^1R^2NH$, the (pre)catalyst and the silane compound, are commercial products.

The amine $R^1R^2NH$ (1 molar equivalent), the (pre)catalyst (from 0.001 to 1 molar equivalent), the silane compound (1 to 3 molar equivalents) and the solvent are introduced into a the Schlenk tube under an inert atmosphere in a glove box and the Schlenk tube is subsequently sealed with a J. Young tap. The concentration of amine and of silane compound in the reaction mixture is approximately 1M (concentration calculated on the basis of the volume of solvent introduced). The order of introduction of the reactants is not important.

The Schlenk tube is subsequently placed under $CO_2$ pressure (from 1 to 3 bar) using a vacuum line and is then heated at a temperature of between 25 and 100° C. until the complete conversion of the amine (reaction from 5 minutes to 72 hours).

Once the reaction is complete, the volatile compounds are removed under reduced pressure and the reaction mixture is purified by chromatography on silica gel. The use of a toluene/hexane mixture as eluant makes it possible to obtain the analytically pure methylated amine.

Alternatively, if the boiling point of the methylated amine of formula (I) is sufficiently low (<200° C.), it can be isolated from the reaction mixture by simple distillation at ambient or reduced pressure.

A body of results is presented below, giving examples of conversions of primary and secondary amines into methylated amines (determined by NMR) using phenylsilane $PhSiH_3$ (sold by Aldrich) and polymethylhydrosiloxane (PMHS) (sold by Aldrich under the reference 176206) as reducing agents, depending on the conditions tested. The structures of the amines and of the (pre)catalysts and of the silanes tested are represented on each occasion.

The reaction scheme is as follows:

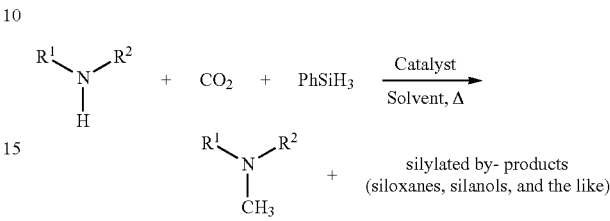

Different (pre)catalysts were tested for their reaction. The results are shown in the following tables.

TABLE 1

(Pre)catalysts involving zinc salts or complexes

| Amine $R^1R^2NH$ | Silane | (Pre)catalyst | Reaction conditions | Product $R^1R^2NCH_3^{(a)}$ |
|---|---|---|---|---|
| O⌒NH (morpholine) | $PhSiH_3$ (2 eq) | IPr (5 mol %) + $Zn(OAc)_2$ (10 mol %) | THF 25° C. (1 h) 100° C. (24 h) | 65% |
| O⌒NH | $PhSiH_3$ (2 eq) | IPr (15 mol %) + [$Zn(OAc)_2$Pyridine] (10 mol %) | THF 25° C. (1 h) 100° C. (24 h) | 89% |
| O⌒NH | $PhSiH_3$ (2 eq) | IPr (5 mol %) + [$ZnEt_2$] (20 mol %) | THF 25° C. (1 h) 100° C. (24 h) | 60% |
| O⌒NH | $PhSiH_3$ (2 eq) | IPr (15 mol %) + [Zn(BDI)Et] (10 mol %) | THF 25° C. (1 h) 100° C. (24 h) | 38% |
| O⌒NH | $PhSiH_3$ (2 eq) | IPr (5 mol %) + $ZnEt_2$ (10 mol %) | THF 25° C. (1 h) 100° C. (72 h) | 90% |
| O⌒NH | $PhSiH_3$ (2 eq) | IPr (5 mol %) + $ZnEt_2$ (10 mol %) | THF 100° C. (72 h) | 65% |
| O⌒NH | $PhSiH_3$ (2 eq) | $ZnEt_2$ (10 mol %) | THF 100° C. (72 h) | 65% |
| iPr₂NH | $PhSiH_3$ (2 eq) | $ZnEt_2$ (5 mol %) | THF 100° C. (90 h) | 35% |

TABLE 1-continued

(Pre)catalysts involving zinc salts or complexes

| Amine $R^1R^2NH$ | Silane | (Pre)catalyst | Reaction conditions | Product $R^1R^2NCH_3$ [a] |
|---|---|---|---|---|
| (iPr)₂NH | PhSiH₃ (2 eq) | IPr (5 mol %) + ZnCl₂ (5 mol %) | THF 100° C. (20 h) | 46% |
| PhN(H)Me | PhSiH₃ (2 eq) | ZnEt₂ (5 mol %) | THF 100° C. (90 h) | 40% |
| Ph—CH₂—NH₂ | PhSiH₃ (2 eq) | IPr (5 mol %) + ZnCl₂ (5 mol %) | THF 100° C. (20 h) | 20% |
| Ph—NH₂ | PhSiH₃ (2 eq) | IPr (5 mol %) + ZnCl₂ (5 mol %) | THF 100° C. (20 h) | 62% |
| MeO-C₆H₄-NH₂ | PhSiH₃ (2 eq) | IPr (5 mol %) + ZnCl₂ (5 mol %) | THF 100° C. (20 h) | 67% |
| nBu-C₆H₄-NH₂ | PhSiH₃ (2 eq) | IPr (5 mol %) + ZnCl₂ (5 mol %) | THF 100° C. (20 h) | 49% |
| F-C₆H₄-NH₂ | PhSiH₃ (2 eq) | IPr (5 mol %) + ZnCl₂ (5 mol %) | THF 100° C. (20 h) | 67% |
| Cl-C₆H₄-NH₂ | PhSiH₃ (2 eq) | IPr (5 mol %) + ZnCl₂ (5 mol %) | THF 100° C. (20 h) | 49% |
| 2,4-Me₂C₆H₃-NH₂ | PhSiH₃ (2 eq) | IPr (5 mol %) + ZnCl₂ (5 mol %) | THF 100° C. (20 h) | 12% |
| Ph₂N—NH₂ | PhSiH₃ (2 eq) | IPr (5 mol %) + ZnCl₂ (5 mol %) | THF 100° C. (20 h) | 10% |
| Ph₂N—NH₂ | PhSiH₃ (2 eq) | IPr (5 mol %) + ZnCl₂ (5 mol %) | THF 100° C. (20 h) | 24% |

It should be noted that "IPr" corresponds to carbene A.
[a] The yields of methylated amines $R^1R^2NCH_3$ have not been optimized. Thus, the modest but encouraging yields obtained for some amines remain to be optimized.

The results show that, under the operating conditions shown in table 1, all the zinc (pre)catalysts are excellent (pre)catalysts as they make it possible to obtain methylated amines with a good yield, indeed even a very good yield (ranging from 35% to 90%).

TABLE 2

(Pre)catalysts involving iron salts or complexes

| Amine R¹R²NH | Silane | (Pre)catalyst | Reaction conditions | Product R¹R²NCH₃ |
|---|---|---|---|---|
| morpholine (O-CH₂-CH₂-NH-CH₂-CH₂) | PhSiH₃ (2 eq) | Fe(BF₄)₂•6H₂O + PP₃ (5 mol %) | THF 100° C. (24 h) | 20% |
| diethylamine | PhSiH₃ (1 eq) | Fe(BF₄)₂•6H₂O + PP₃ (5 mol %) | THF 100° C. (24 h) | 5% |
| piperidine | PhSiH₃ (1 eq) | Fe(BF₄)₂•6H₂O + PP₃ (5 mol %) | THF 100° C. (24 h) | 15% |
| N-methylaniline | PhSiH₃ (1 eq) | Fe(BF₄)₂•6H₂O + PP₃ (5 mol %) | THF 100° C. (24 h) | 25% |
| diphenylamine | PhSiH₃ (1 eq) | Fe(BF₄)₂•6H₂O + PP₃ (5 mol %) | THF 100° C. (24 h) | 20% |
| morpholine | PhSiH₃ (2 eq) | Fe(BF₄)₂•6H₂O + PP₃ (5 mol %) | THF 100° C. (70 h) | 35% |
| diethylamine | PhSiH₃ (1 eq) | Fe(acac)₃ (3.5 mol %) + PP₃ (5 mol %) | THF 100° C. (24 h) | 25% |
| diisopropylamine | PhSiH₃ (1 eq) | Fe(acac)₃ (3.5 mol %) + PP₃ (5 mol %) | THF 100° C. (24 h) | 45% |
| piperidine | PhSiH₃ (1 eq) | Fe(acac)₃ (3.5 mol %) + PP₃ (5 mol %) | THF 100° C. (24 h) | 5% |

The results show that, under the operating conditions shown in table 2, the most active (pre)catalysts result from the mixtures Fe(acac)₃+PP₃ and Fe(BF₄)₂.6H₂O+PP₃. For the other (pre)catalysts, an optimization of the operating conditions may be envisaged.

TABLE 3

(Pre)catalyst involving an organic molecule

| Amine R¹R²NH | Silane | (Pre)catalyst | Reaction conditions | Product R¹R²NCH₃ |
|---|---|---|---|---|
| N-methylaniline | PhSiH₃ (1 eq) | IPr (5 mol %) | THF 70° C. (24 h) | 50% |

Under the operating conditions shown in table 3, the methylated amine is obtained with a good yield.

TABLE 4

(Pre)catalysts involving copper salts or complexes

| Amine R¹R²NH | Silane | (Pre)catalyst | Reaction conditions | Product R¹R²NCH₃ |
|---|---|---|---|---|
| morpholine | PMHS (3 eq) | Cu(OAc)₂(H₂O) (5 mol %) dppb (7.5 mol %) | THF 100° C. (72 h) | 40% |
| morpholine | PhSiH₃ (2 eq) | Cu(OAc)₂(H₂O) (5 mol %) dppb (7.5 mol %) | THF 100° C. (72 h) | 20% |

TABLE 4-continued (Pre)catalysts involving copper salts or complexes

| Amine R¹R²NH | Silane | (Pre)catalyst | Reaction condtions | Product R¹R²NCH₃ |
|---|---|---|---|---|
|  | PMHS (3 eq) | Cu(OAc)₂(H₂O) (5 mol %) dppb (7.5 mol %) | THF 100° C. (72 h) | 25% |
|  | PhSiH₃ (2 eq) | Cu(OAc)₂(H₂O) (5 mol %) dppb (7.5 mol %) | THF 100° C. (72 h) | 20% |

The results show that, under the operating conditions shown in table 4, phenylsilane PhSiH₃ can be replaced by a polysilane (silane of polymeric structure), polymethylhydrosiloxane (PMHS). In the case of PMHS, the number of molar equivalents of silane is understood as the number of molar equivalents of monomer unit (MeSiHO).

The abbreviations used are represented below:

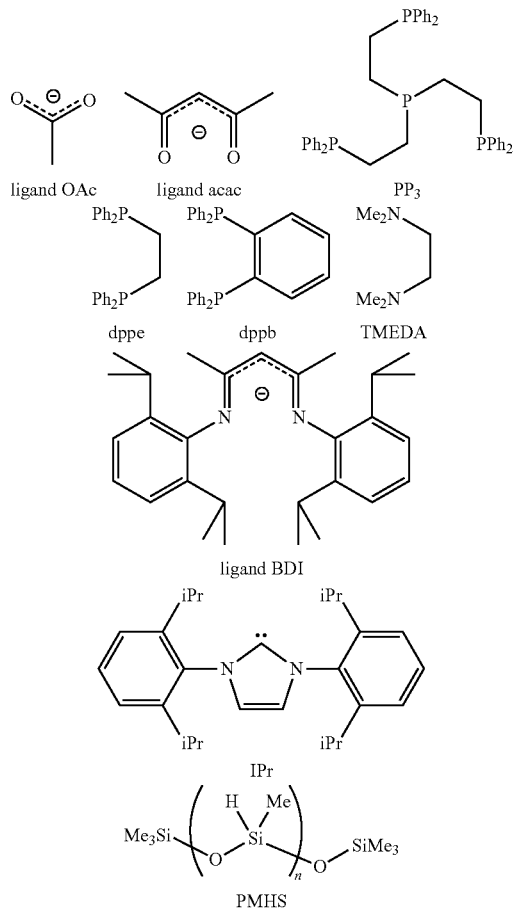

These results show that the preparation of methylated amines by the process of the invention is sufficiently flexible to efficiently convert a great variety of secondary, aliphatic, aromatic and heterocyclic amines, both with metal salts and complexes and with organic molecules as (pre)catalyst, under mild conditions of CO₂ pressures and reaction temperatures.

The invention claimed is:

1. A process for the preparation of methylated amines of formula (I):

$$\begin{array}{c} R^1 \\ \diagdown \\ N-CH_3 \\ \diagup \\ R^2 \end{array} \quad (I)$$

in which:
R¹ and R² represent, independently of one another,
a hydrogen atom, an alkyl group, an aryl group, or a heteroaryl group, said alkyl, aryl, and heteroaryl groups optionally being substituted, or
R¹ and R², taken together with the nitrogen atom to which they are bonded, form an optionally substituted heterocycle,
R¹ and R² optionally comprise an H, C, N, O, F, Si and/or S as defined below;
H represents a hydrogen atom ($^1$H), deuterium ($^2$H) or tritium ($^3$H);
C represents a carbon atom ($^{12}$C) or a $^{11}$C, $^{13}$C or $^{14}$C isotope;
N represents a nitrogen atom ($^{14}$N) or a $^{15}$N isotope;
O represents an oxygen atom ($^{16}$O) or an $^{18}$O isotope;
F represents a fluorine atom ($^{19}$F) or a $^{18}$F isotope;
Si represents a silicon atom ($^{28}$Si) or a $^{29}$Si or $^{30}$Si isotope;
S represents a sulfur atom ($^{32}$S), or a $^{33}$S, $^{34}$S or $^{36}$S isotope;
comprising a step of reacting an amine of formula (II), in which R¹ and R² and N are as defined above:

$$\begin{array}{c} R^1 \\ \diagdown \\ H-N \\ \diagup \\ R^2 \end{array} \quad (II)$$

with CO₂, in which C and O are as defined above, in the presence of a catalyst and of a silane compound of formula (III):

$$\begin{array}{c} R^3 \\ \diagdown \\ H-Si-R^4 \\ \diagup \\ R^5 \end{array} \quad (III)$$

in which:
H is as defined above,
R³, R⁴ and R⁵ represent, independently of one another,
a hydrogen atom, an alkyl group, an alkoxy group, an aryl group, a silyl group or a siloxy group, said alkyl, alkoxy, silyl, siloxy, and aryl groups optionally being substituted.

2. The process as claimed in claim 1, wherein the catalyst is selected from the group consisting of organic catalysts and metal catalysts, the metal catalysts being chosen from metal salts or metal complexes.

3. The process as claimed in claim 2, wherein the organic catalyst is:
- a secondary or tertiary amine selected from the group consisting of triazabicyclodecene (TBD), N-methyltriazabicyclodecene (MeTBD), 1,8-diazabicyclo[5.4.0]undec-7-ene (DBU), trimethylamine, triethylamine, piperidine, 4-dimethylaminopyridine (DMAP), 1,4-diazabicyclo[2.2.2]octane (DABCO), proline, phenylalanine, a thiazolium salt and N-diisopropylethylamine (DIPEA or DIEA), or
- an N-heterocyclic carbene resulting from an imidazolium salt selected from the group consisting of 1,3-bis(2,6-diisopropylphenyl)-1H-imidazol-3-ium (carbene A), 1,3-bis(2,6-diisopropylphenyl)-4,5-dihydro-1H-imidazol-3-ium (carbene C), 1,3-bis(2,4,6-trimethylphenyl)-1H-imidazol-3-ium (carbene B), 1,3-bis(2,4,6-trimethylphenyl)-4,5-dihydro-1H-imidazol-3-ium (carbene D), 4,5-dichloro-1,3-bis(2,6-diisopropylphenyl)-1H-imidazol-3-ium (carbene E), 1,3-di(tert-butyl)-1H-imidazol-3-ium (carbene F) and 1,3-di(tert-butyl)-4,5-dihydro-1H-imidazol-3-ium salts, said salts being in the form of chloride salts.

4. The process as claimed in claim 2, wherein the metal catalyst is selected from the group consisting of metal salts or complexes of:
- metals chosen from boron, silicon, aluminum, gallium, tin or indium;
- alkali metals chosen from sodium or potassium;
- alkaline earth metals chosen from magnesium or calcium;
- transition metals selected from the group consisting of nickel, iron, cobalt, zinc, copper, rhodium, ruthenium, platinum, palladium and iridium; and
- rare earth metals chosen from lanthanum, cerium, praseodymium or neodymium.

5. The process as claimed in claim 1, wherein the reaction is carried out under a $CO_2$ pressure of between 1 and 50 bar, limits included.

6. The process as claimed in claim 1, wherein the reaction is carried out at a temperature of between 25 and 150° C., limits included.

7. The process as claimed in claim 1, wherein the reaction is carried out for a period of time of 5 minutes to 72 hours, limits included.

8. The process as claimed in claim 1, wherein the reaction is carried out in a mixture of at least two solvent(s) selected from the group consisting of:
- ethers,
- hydrocarbons,
- nitrogenous solvents,
- sulfoxides, and
- alkyl halides.

9. The process as claimed in claim 1, wherein the solvent is the amine of formula (II).

10. The process as claimed in claim 1, wherein the molar ratio of the silane compound of formula (III) to the amine of formula (II) is from 1 to 10, limits included.

11. The process as claimed in claim 1, wherein the amount of catalyst is from 0.001 to 1 molar equivalent, limits included, with respect to the amine of formula (II).

12. A process for the manufacture of vitamins, pharmaceutical products, adhesives, acrylic fibers, synthetic leather, pesticides and fertilizers comprising a step of preparing methylated amines of formula (I) by reacting an amine of formula (II) with $CO_2$ in the presence of a catalyst and of a silane compound of formula (III) as claimed in claim 1.

13. A process for the manufacture of tracers and radioactive tracers, wherein the process comprises a step of preparation of labeled methylated amines of formula (I) as claimed in claim 1.

14. The process as claimed in claim 1, wherein the reaction is carried out under a $CO_2$ pressure of between 1 and 30 bar, limits included.

15. The process as claimed in claim 1, wherein the reaction is carried out under a $CO_2$ pressure of between 1 and 10 bar, limits included.

16. The process as claimed in claim 1, wherein the reaction is carried out at a temperature of between 50 and 125° C., limits included.

17. The process as claimed in claim 1, wherein the reaction is carried out for a period of time of 15 minutes to 48 hours.

18. The process as claimed in claim 1, wherein the reaction is carried out in a mixture of at least two solvent(s) selected from the group consisting of diethyl ether, THF, benzene, toluene, pyridine, acetonitrile, dimethyl sulfoxide, chloroform, and methylene chloride.

* * * * *